United States Patent [19]

Duc et al.

[11] Patent Number: 5,144,047

[45] Date of Patent: Sep. 1, 1992

[54] PROCESS FOR THE PRODUCTION OF TETRONIC ACID ALKYL ESTERS

[75] Inventors: Laurent Duc, Chermignon; John McGarrity, Visp, both of Switzerland

[73] Assignee: Lonza Ltd., Gampel/Valais, Switzerland

[21] Appl. No.: 554,372

[22] Filed: Jul. 19, 1990

[30] Foreign Application Priority Data

Jul. 20, 1989 [CH] Switzerland ............ 2706/89

[51] Int. Cl.$^5$ ............................................ C07D 307/00
[52] U.S. Cl. ................................................ 549/429
[58] Field of Search .......................................... 549/429

[56] References Cited

U.S. PATENT DOCUMENTS

2,571,212 10/1951 Croxall et al. ................ 260/484
2,864,852 12/1958 Jones ................ 260/465.4
4,812,593 3/1989 Hoelderich et al. ................ 560/183

FOREIGN PATENT DOCUMENTS

216324 9/1986 European Pat. Off. ............ 549/429
2845037 10/1978 Fed. Rep. of Germany ...... 549/429

OTHER PUBLICATIONS

Pelter et al., J. Chem. Soc. Perkin Trans. I, (1987), p. 717 ff.
Pelter et al., Tetrahedron Letters, No. 18, (1979), p. 1627 ff.

*Primary Examiner*—Mary C. Lee
*Assistant Examiner*—Robert C. Whittenbaugh
*Attorney, Agent, or Firm*—Fisher, Christen & Sabol

[57] ABSTRACT

Tetronic acid alkyl esters are produced at a higher temperature by a ring closure of 4-halo-3-alkoxy-2-butene carboxylic acids. The tetronic acid alkyl esters are reacted by in acid hydrolysis in tetronic acid.

21 Claims, No Drawings

PROCESS FOR THE PRODUCTION OF TETRONIC ACID ALKYL ESTERS

BACKGROUND OF THE INVENTION

1. Field of the Invention

The invention relates to a new process for the production of tetronic acid alkyl esters, and to a new process for producing tetronic acid for such esters.

2. Background Art

Tetronic acid alkyl esters are known compounds, which can be used as valuable intermediate products, e.g., for pharmaceutical agents. See for this purpose, e.g., Pelter et al., J. Chem. Soc. Perkin Trans. I, (1987), p. 717 ff., or Pelter et al., Tetrahedron Letters, No. 18, (1979), p. 1627 ff.

Production of tetronic acid methyl ester is known, e.g., from West German PS 2,845,037, in which a 4-bromo-3-methoxybut-2-ene carboxylic acid lower alkyl ester is cyclized in an organic solvent with a Lewis acid, e.g., zinc dibromide. Yields between 70 and 80 percent are described. But from an ecological viewpoint, it is a disadvantage that heavy metal catalysts, which cannot be recycled, must be used in such process. The reworking of the process with the appropriate 4-chlorine analog, moreover, has shown that the yield, significantly lower than indicated, must be estimated at about 50 percent.

BROAD DESCRIPTION OF THE INVENTION

An object of the invention is to provide a process for the production of tetronic acid alkyl esters. Another object of the invention is to provide a process for the use of tetronic acid alkyl esters for the production of tetronic acid, an additional important structural element for the syntheses of numerous active ingredients. Another object of the invention is to provide a process that on the one hand is ecologically safer and on the other hand provides high yields of a high-quality product. Other advantages and objects of the invention are set out herein or are obvious herefrom to one skilled in the art.

The objects and advantages of the invention are achieved by the process of the invention.

The invention involves a process for the production of tetronic acid alkyl esters of the formula:

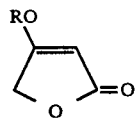

wherein R is an alkyl group with 1 to 6 C atoms. The process includes cyclizing a 4-halo-3-alkoxy-2-butene carboxylic acid lower alkyl ester of the general formula:

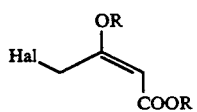

wherein Hal is chlorine or bromine, and R has the above-named meaning, at a temperature between 190° and 260° C. Preferably the reaction is performed at a temperature between 200° and 220° C. Preferably the reaction is performed under an inert gas atmosphere.

Preferably the resultant tetronic acid alkyl ester is obtained from the reaction mixture by distillation.

The invention also involves using the tetronic acid alkyl ester, produced according to the invention process, for the production of tetronic acid. Preferably the tetronic acid alkyl ester is subjected to an acid hydrolysis. Preferably the acid hydrolysis is performed in acetic acid with hydrogen chloride or hydrogen bromide.

DETAILED DESCRIPTION OF THE INVENTION

The initial compounds of the process according to the invention are the 4-halo-3-alkoxy 2-butene carboxylic acid lower alkyl esters of general formula:

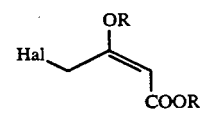

wherein Hal is chlorine or bromine and R is an alkyl group with 1 to 6 C atoms, which can be produced in a simple way, e.g., according to European Published Patent Application No. 216,324 from commercially available haloacetoacetic esters. The 4-chloro-3-($C_1$–$C_4$)-alkoxy-2-butene carboxylic acid-($C_1$–$C_4$) alkyl esters are preferably used.

The ring closure to the appropriate tetronic acid alkyl ester of general formula:

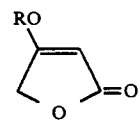

wherein R has the above-named meaning, takes place at a temperature between 190° and 260° C., preferably at a temperature between 200° and 220° C. The characteristic feature of the reaction is that no solvent is used. The reaction advantageously is performed in an inert gas atmosphere, preferably with nitrogen, while excluding atmospheric oxygen. According to experience, after a reaction time of about 1 to 6 hours, the appropriate tetronic acid alkyl ester can be isolated from the reaction mixture, suitably by distillation. The attainable yields generally are over 90 percent; and the purity of the product is around 99 percent.

In a simple way, according to the invention, the resultant tetronic acid alkyl esters are converted in practically quantitative yield to the tetronic acid. For this purpose, the tetronic acid alkyl ester is subjected to an acid hydrolysis, suitably with hydrogen chloride or hydrogen bromide in acetic acid. With the use of hydrogen chloride in acetic acid, a temperature range of 50° to 140° C. and a pressure of 2 to 8 bars have been shown as suitable conditions of hydrolysis. With the use of hydrogen bromide, one can use standard pressure and a temperature between 30° and 120° C. After a reaction time of about 3 to 8 hours, the tetronic acid can be isolated in a standard way in excellent quality.

EXAMPLE 1

Production of Tetronic Acid Methyl Ester 195.1 g (1.19 mol) of 4-chloro-3-methoxy-2E-butene carboxylic acid methyl ester was stirred in an $N_2$ atmosphere for 5 hours at a temperature of 200° to 205° C. The resultant gaseous chloromethane was trapped. Then, the tetronic acid methyl ester product was distilled out of the resultant reaction mixture at 18 mbars and 130° to 131° C. 127.4 g (82.5 percent) of the tetronic acid methyl ester product with a purity of 98.2 percent (GC) and a mp of 63° to 64° C., was obtained.

EXAMPLE 2

Production of Tetronic Acid Ethyl Ester 38.6 g (0.2 mol) of 4-chloro-3-ethoxy-2E-butene carboxylic acid ethyl ester was stirred in N₂ atmosphere for 1.5 hours at a temperature of 210° to 220° C. The resultant chloroethane was trapped. Then the tetronic acid ethyl ester product was distilled out of the reaction mixture at 16 mbars and 135° to 137° C. 22.5 g (87.4 percent) of the tetronic acid ethyl ester product with a content of 99.5 percent (GC) was obtained.

EXAMPLE 3

Production of Tetronic Acid-n-butyl Ester 20.9 g (0.084 mol) of 4-chloro-3-n-butoxy-2E-butene carboxylic acid butyl ester was stirred in N₂ atmosphere for 1.5 hours at a temperature of 220° C. The resultant chlorobutane was trapped. The tetronic acid-n-butyl ester product was distilled out of the reaction mixture at 0.05 mbar and 87° to 89° C. 12.4 g (94 percent) of the tetronic acid-n-butyl ester product with a content of 99 percent was obtained.

Comparison Example According to West German PS 2,845,037

20 g (0.12 mol) of 4-chloro-3-methoxy-2E-butene carboxylic acid methyl ester was introduced in 20 ml of p-xylene with 0.1 g of zinc bromide and refluxed. The course of the reaction was controlled with GC. After 7 hours, 0.1 g of zinc bromide again was added; after 16 hours, 2 g of zinc bromide again was added. After 24 hours, a 90 percent conversion of educt was able to be determined (GC). Then the p-xylene was distilled off. The residue was extracted with a mixture of 12 ml of chloroform and 48 ml of ether. The extract thereupon was cooled to −27° C. In this way, 7 g (51.1 percent) of crude tetronic acid methyl ester was precipitated out. The latter was purified by distillation at 18 mbars and 130° to 131° C. As a result, 6.2 g (45.5 percent) of tetronic acid methyl ester was obtained.

EXAMPLE 4

Production of Tetronic Acid 10 g (0.088 mol) of tetronic acid methyl ester was introduced in an autoclave at 5° C. in acetic acid saturated with hydrogen chloride. The reaction mixture was stirred for 6 hours at a temperature of 80° C. and a pressure of 4 bars. After cooling off to room temperature, it was evaporated to dryness, the residue was taken up to 30 ml of methylene chloride, the suspension was cooled to 10° C. and filtered, and the product was dried. 8 g (91 percent) of the tetronic acid product with a content of 99.3 percent (HPLC), and having a mp 135° to 136° C. (decomposition), was obtained.

What is claimed is:

1. Process for the production of a tetronic acid alkyl ester of the formula:

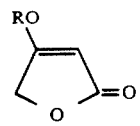

wherein R is an alkyl group with 1 to 6 C atoms, consisting essentially of cyclizing a 4-halo-3-alkoxy-2-butene carboxylic acid lower alkyl ester of the formula:

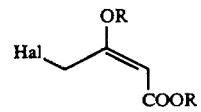

wherein Hal is chlorine or bromine, and R has the above-named meaning, at a temperature between 190° and 260° C.

2. The process according to claim 1 wherein the reaction is performed at a temperature between 200° and 220° C.

3. The process according to claim 2 wherein the reaction is performed under an inert gas atmosphere.

4. The process according to claim 3 wherein the resultant tetronic acid alkyl ester is obtained from the reaction mixture by distillation.

5. The process according to claim 1 wherein the reaction is performed under an inert gas atmosphere.

6. The process according to claim 1 wherein the resultant tetronic acid alkyl ester is obtained from the reaction mixture by distillation.

7. The process according to claim 3 wherein the inert gas is nitrogen.

8. The process according to claim 3 wherein atmospheric oxygen is excluded a the same time.

9. Process for the production of tetronic acid, consisting essentially of cyclizing a 4-halo-3-alkoxy-2-butene carboxylic acid lower alkyl ester of the formula:

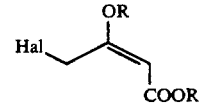

wherein Hal is chlorine or bromine, and R has the above-named meaning, at a temperature between 190° and 260° C., to obtain a tetronic acid alkyl ester of the formula:

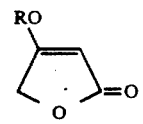

wherein R is an alkyl group with 1 to 6 C atoms, and converting the tetronic acid alkyl ester to tetronic acid.

10. The process according to claim 9 wherein the tetronic acid alkyl ester is subjected to an acid hydrolysis to achieve the conversion.

11. The process according to claim 10 wherein the acid hydrolysis is performed in acetic acid with hydrogen chloride or in acetic acid with hydrogen bromide.

12. The process according to claim 1 wherein no solvent is present during the cyclization.

13. The process according to claim 9 wherein no solvent is present during the cyclization.

14. Process for the production of a tetronic acid alkyl ester of the formula:

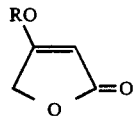

wherein R is an alkyl group with 1 to 6 C atoms, consisting of cyclizing a 4-halo-3-alkoxy-2-butene carboxylic acid lower alkyl ester of the formula:

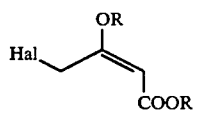

wherein Hal is chlorine or bromine, and R has the above-named meaning, at a temperature between 190° and 260° C.

15. The process according to claim 14 wherein Hal is chlorine.

16. The process according to claim 14 wherein Hal is bromine.

17. Process for the production of a tetronic acid alkyl ester of the formula:

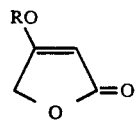

wherein R is an alkyl group with 1 to 6 C atoms, consisting of cyclizing a 4-halo-3-alkoxy-2-butene carboxylic acid lower alkyl ester of the formula:

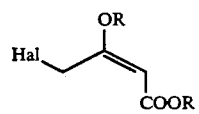

wherein Hal is chlorine or bromine, and R has the above-named meaning, at a temperature between 190° and 260° C. under an inert gas atmosphere.

18. The process according to claim 17 wherein the inert gas is nitrogen.

19. The process according to claim 17 wherein atmospheric oxygen is excluded at the same time.

20. The process according to claim 17 wherein Hal is chlorine.

21. The process according to claim 17 wherein Hal is bromine.

* * * * *